United States Patent
Sowerby

Patent Number: 5,509,426
Date of Patent: Apr. 23, 1996

[54] ARM BRACE

[76] Inventor: Frederick O. Sowerby, 360 N. Arroyo Grande, #411, Henderson, Nev. 89014

[21] Appl. No.: 257,210

[22] Filed: Jun. 9, 1994

[51] Int. Cl.⁶ .................... A61F 5/37; A61F 5/00
[52] U.S. Cl. .............................. 128/878; 602/12
[58] Field of Search ................... 602/5, 12, 15, 602/16, 20, 21; 128/877, 878, 879, 881

[56] References Cited

U.S. PATENT DOCUMENTS

| | | |
|---|---|---|
| D. 266,345 | 9/1982 | Bigham et al. . |
| D. 270,556 | 9/1983 | Kneisley . |
| D. 275,219 | 8/1984 | Scales, Jr. . |
| D. 278,566 | 4/1985 | Gustafson . |
| D. 285,821 | 9/1986 | Kneisley . |
| D. 287,641 | 1/1987 | Schaefer . |
| D. 323,216 | 1/1992 | Russell et al. . |
| D. 323,217 | 1/1992 | Holden . |
| D. 333,520 | 2/1993 | Mann . |
| D. 340,155 | 10/1993 | Koziol . |
| D. 340,524 | 10/1993 | Russell . |
| 1,431,915 | 10/1922 | Barr .................... 128/881 |
| 1,772,601 | 8/1930 | Dunham ................ 128/881 |
| 2,704,069 | 3/1955 | Donelan ................ 128/881 |
| 3,028,858 | 4/1962 | Cutler .................. 602/20 |
| 3,698,389 | 10/1972 | Guedel .................. 602/20 |
| 4,254,953 | 3/1981 | Marchetti .............. 602/20 |
| 4,285,337 | 8/1981 | Cosentino . |
| 4,523,586 | 6/1985 | Couri . |
| 4,530,351 | 7/1985 | Gordon . |
| 4,705,271 | 11/1987 | Mondloch et al. . |
| 4,736,312 | 4/1988 | Dassler et al. . |
| 4,765,320 | 8/1988 | Lindemann et al. . |
| 4,766,890 | 8/1988 | Hollrah . |
| 4,842,274 | 6/1989 | Oosthuizen et al. . |
| 4,884,561 | 12/1989 | Letson .................. 602/20 |
| 4,900,013 | 2/1990 | Rodgers, Jr. . |
| 4,941,479 | 7/1990 | Russell et al. . |
| 4,977,890 | 12/1990 | Mann . |
| 5,027,794 | 7/1991 | Pyle . |
| 5,058,576 | 10/1991 | Grim et al. . |
| 5,121,743 | 6/1992 | Bishop . |
| 5,170,777 | 12/1992 | Reddy et al. . |
| 5,179,939 | 1/1993 | Donovan et al. . |

*Primary Examiner*—Michael A. Brown
*Attorney, Agent, or Firm*—Quirk & Tratos

[57] ABSTRACT

A training brace is provided for retaining the position of an arm of an athlete. The brace comprises mating first and second arm engaging members, means for securing the members together and to the arm, and stop means for limiting the position the arm of the wearer may achieve. The members are preferably concave and each include a section which engages the upper arm and the forearm and which when connected, surround the arm. The members are hingedly connected along one edge, and are securely mated to surround the arm of a wearer with connecting straps which encompass the members. Stop means are provided for preventing the forearm and upper arm of the wearer, as measured at the elbow, from achieving an angle of greater than about 90 degrees.

6 Claims, 1 Drawing Sheet

5,509,426

ARM BRACE

FIELD OF THE INVENTION

The present invention relates to an athletic training device. In particular, the present invention relates to a brace which is used to restrain an arm of a runner in a fixed position.

BACKGROUND OF THE INVENTION

A need has existed for some time for a training aid for competitive athletes by which the athlete learns to maintain proper arm position when running.

It has been found that in order for an athlete to maximize running speed, proper arm position is necessary. This is true whether the runner is a professional or merely an amateur athlete, and whether the distance to be run is short, in the case of a sprint, or long, in the case of a marathon.

In particular, it is advantageous for a runner to keep his arms and hands up away from the area in which his legs are moving. When the runner's legs are constantly moving up and down, positioning of the arms near the lower torso of the body, or near the legs, interferes with the full range of motion of the legs. Even if a runner's legs do not actually touch his arms, when the arms are carried low, the runner naturally raises his legs just short of his arms or hands in order to avoid contact, resulting in decreased speed.

In order for a runner to maximize the results of his effort, he must raise and lower his legs to a position in which the thigh is approximately perpendicular to his body. In order to prevent the upward movement of the legs from being cut short, runners are instructed to keep their arms out of the way of their legs.

Preferably, the forearm of the runner is bent at an angle of approximately 90 degrees with respect to the upper arm. In this position, the forearm is pointed outwardly at approximately a right angle with respect to the upper arm, and does not extend downwardly in a fashion which can cause interference with the full range of motion of the legs.

Unfortunately, up until this time, there has been no successful means for training an athlete to maintain this desired arm position when running. Most training methods simply involve a coach informing the runner that his or her arm positioning is incorrect, and instructing the runner to raise his forearm with respect to the upper arm to achieve the correct arm positioning.

There remains a need for a positive structural training aid for athletes which aids the athlete in learning the correct arm position while running.

SUMMARY OF THE INVENTION

In order to overcome the above stated problems and limitations, an arm brace is provided to maintain a runner's arm in a predetermined fixed orientation. The arm brace includes section which releasably engage the upper and lower arm members, and a connecting portion that maintains the elbow at a fixed angle.

The sections are preferably molded from plastic, and comprise mating concave halves such that when the members are connected, they surround and enclose the arm. Preferably, the mating sections or members are hingedly connected along one edge, so that the sections may be opened and closed in clam-shell fashion for insertion and removal of the arm.

Means for connecting comprising straps are used to secure the members in a closed position about the arm. The straps preferably encircle the brace, and are locked into place using Velcro tabs.

Lastly, stop means are used to limit the angle of the arm of the wearer with the brace installed. In particular, as stated above, it is desirable to have the angle between the upper arm and forearm, as measured at the elbow, at an angle of less than about 105 degrees, in the range of 75–105 degrees, and more preferably about 90 degrees.

In the instant case, maintenance of the desired arm angle can be achieved in two manners. First, the first and second members are preferably molded such that the angle between the upper and forearm engaging sections thereof are at the desired angle. Alternatively, the brace includes upper and lower arm-encircling members which are connected by an angle-controlling stop or strut which prevents the user from being able to extend his arm beyond the desired position. As used herein, the "upper arm" means any portion of the arm between the elbow and the shoulder, and "lower arm" or "forearm" means any portion of the arm between the elbow and wrist.

Further objects, features, and advantages of the present invention will become apparent from the detailed description of the drawings which follows, when considered with the attached figures.

DETAILED DESCRIPTION OF THE PREFERRED EMBODIMENT

Figure 1:
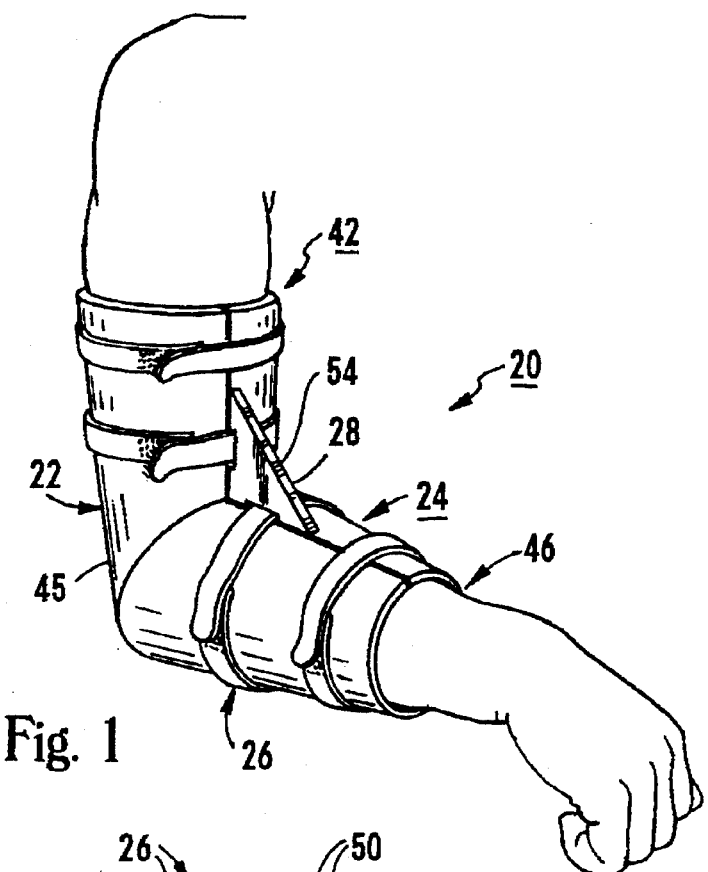
FIG. 1 is a perspective view of the brace of the present invention placed on the arm of a user.
Figure 2:
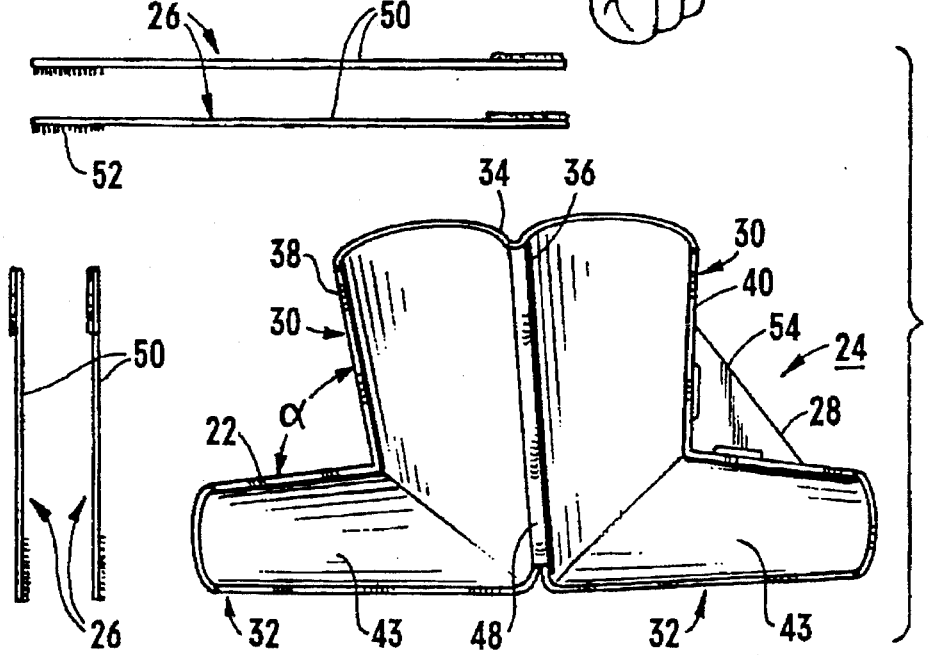
FIG. 2 is an exploded view of the brace of FIG. 1, illustrating hingedly connected first and second arm-engaging members and means for securing them in a closed position.

FIGS. 1 and 2 illustrates a training brace 20 of the present invention. As illustrated, the brace 20 preferably comprises first and second arm engaging members 22, 24, means for securing the members 26, and most preferably further includes stop means 28 for limiting the angle of the arm of the user at the elbow. It is understood that the brace 20 described and illustrated is for the right arm of a user, and that a matching brace 20 mirroring the brace for the right arm can be, and preferably is, designed for placement on the left arm of the user, whereby both arms are appropriately positioned during training.

The first and second arm engaging members 22, 24 generally comprise concave members having a shape which matches the shape of an arm. In particular, the members 22, 24 preferably both include an upper arm engaging section 30, and a lower arm engaging section 32. As illustrated, the engaging members 22, 24 both include an inner surface 43 for engaging the arm of the wearer, and an outer surface 45. The members 22, 24 also include a first inside edge 34, 36 and an outer edge 38, 40. Further, the brace 20 includes a first end 42 and a second end 46.

Each member 22, 24 is preferably concave, whereby the inner surface 43 of each of the members 22, 24 contacts and surrounds or cradles a portion of the arm of the wearer. In the preferred form, the interior shape of the members 22, 24 is chosen such that when the members 22, 24 are placed about an arm, they completely surround the arm of the wearer. Thus, in the preferred form, the opening at the first end 42 of the brace 20 when the members 22, 24 are connected is preferably about 3 to 8 inches, and most preferably about 5 inches in diameter. The opening which is created at the second end 46 of the brace 20 when the members 22, 24 are connected is preferably about 1.5 to 5 inches, and most preferably about 3.5 inches in diameter.

The upper arm engaging section 30 preferably extends upwardly a distance such that when worn by a user, the member 22, 24 contacts at least a portion of the upper arm above the elbow. In the preferred embodiment, the section 30 extends upwardly a sufficient distance to contact the upper arm of a user at least 3 to 9 inches above the elbow of the user, and most preferably about 8 inches as measured along the back of the arm, and 4 inches as measured along the front of the arm of the wearer.

The lower arm engaging section 32 preferably extends from its intersection with the upper arm engaging section 30 a sufficient distance to engage a portion of the forearm past the elbow. Preferably, the lower arm engaging section 32 extends at least 3 to 9 inches along the forearm of the user, and most preferably about 8 inches along the bottom of the forearm, and about 4 inches as measured along the top of the forearm.

The brace 20, and thus the members 22, 24, may be made of any number of materials, such as plastic, metal or even a semi-rigid fabric. Most preferably, the brace 20 is made of a fairly rigid plastic material to prevent the user from flexing the brace 20. Of course, when the brace 20 is made of plastic or metal or a similar rigid material, the brace may be quite uncomfortable to wear. It is possible for the brace 20 to be made of a somewhat flexible material such as cloth, especially when such has some structural rigidity.

As illustrated, the members 22, 24 preferably are molded to engage an arm when the forearm and upper arm thereof are at an angle $\alpha$ (as indicated in FIG. 1) of about 75–105 degrees, preferably less than 95 degrees, and most preferably about 90 degrees, as measured at the inside of the elbow. Of course, when the members 22, 24 are made of a somewhat flexible material, it is only important that the members 22, 24 be fashioned such that this arm position, along with the aid of stop means 28 described below, is achieved.

It is possible to render the brace 20 more comfortable when made of a fairly rigid material by inserting a thin padding material onto the inner surface 43 of each of the members 22, 24. This padding should not be of a thickness, however, so that the wearer of the brace 20 can move the arm out of the desired position through compression of the padding.

Further, to allow the brace 20 to "breathe" and allow air therethrough to prevent the arm from becoming hot, it is possible to place one or more through holes in the members 22, 24. In fact, it may be that these holes constitute a majority of the area of the brace 20, as surrounded by a thin webbing which comprises the members 22, 24.

While it is preferred that the first and second arm engaging members 22, 24 comprise mating halves which surround the arm of the user, it is possible for the engaging members to take on a variety of other arm engaging shapes. For example it is possible for the members 22, 24 to simply comprise bars or rods, or narrow flat plates, in for example, an "L" shape.

Further, it is possible to have only one member in such an instance, where the single member encompasses a significant portion of the arm, as where the member is fairly tubular but is flexible in the circumferential direction and includes a slit which allows the member to be opened and the arm placed therein. The member may also only contact a minor portion of the arm, but include straps or other means for securing it to the arm. In such instances, the means for connecting described below may be construed broadly to mean means for connecting the brace to the arm.

As illustrated in the preferred embodiment, in order to facilitate the easy location of the brace 20 on the arm of a user, the first and second arm engaging members 22, 24 are preferably concave. Further, the members 22, 24 are hingedly connected to each other along their entire length. In particular, at least one hinge 48 is preferably located between the inside edges 34, 36 of the first and second arm engaging members 22, 24, preferably at the upper arm engaging section 30 thereof. Of course, it is possible to hingedly connect the device along any other mating portions of the members 22, 24.

The hinge 48 may comprise a metal or plastic member which is attached to each member 22, 24. Most preferably, the hinge 48 comprises a flexible piece of plastic which is molded as part of, and between, each of the members 22, 24, when the members 22 are made of plastic and molded as well.

It should be understood that it is not necessary, but only preferred, to have a hinged connection between the members. This connection simply aids the wearer in installing the brace, as no difficulty arises in aligning the two members. Further, when so connected the members cannot be separated and lost or mixed with other members which might not be of the same size.

In the preferred embodiment, means for connecting 26 the free edges of each of the first and second arm engaging members 22, 24 and closing them about the arm are provided. In general the securing means 26 are used to connect the brace 20 to the arm. In the preferred embodiment where the brace 20 comprises members 22, 24 which surround the arm, the means 26 connect the brace 20 to the arm by locking or connecting the members 22, 24 together. The means 26 are preferably used to hold the members 22, 24 secure in mating fashion against one another when the brace 20 is worn by a user. The means 26 preferably comprises a strap 50 having means 52. The strap 50 is designed to encompass the brace 20 when worn, and thus has a length greater than the diameter of the brace 20 at the particular position where used. For example, the strap 50 need only be 3 to 4 inches in diameter if placed near the second end 46 of the brace 20, and may need to be 6" or more if used near the first end 42 of the brace 20.

The straps 50 are preferably fairly narrow, and may be made of any type of material. For example, the straps 50 may be made of leather or cloth. Most importantly, the material the strap 50 is made of should be wear resistant, lightweight, and strong.

As illustrated, when the connecting means 26 comprises straps 50, it is preferred that at least 4 straps 50 be used to secure the members 22, 24. Of course, any number of such straps 50, from 1 or 2 to as many as 6 or 7, may be used, depending on the size of the brace 20 and the fastening force required.

As noted, the straps 50 preferably include fastening means 52. In the preferred form, these means 52 comprise corresponding hook and loop fasteners, such as the type available under the name Velcro™ pieces located on each end of the straps 50, such that the ends of the straps 50 may be connected to one another. Of course, the exact size of the Velcro™ means 52 can vary depending on the length of the strap 50 and desired overlap.

It is understood that one skilled in the art could replace the hook and loop fastening means 52 with any number of fastening means known, such as snaps, hooks, or the like. Further, it is possible for the means for connecting 26 to comprise something other than connecting straps 50. For example, hooks or engaging locking means may be connected directly to each member 22, 24 for interconnection of the members 22, 24, or even a cord may be wrapped around the members 22, 24 to hold them together.

Most importantly, stop means 38 are preferably provided for limiting the angle between the forearm and upper arm of the wearer at the elbow. In the case of a brace 20 in which the members 22, 24 are made of a rigid material such as metal or rigid plastic, the members 22, 24 may simply be molded or manufactured such that the upper and lower arm engaging sections 30, 32 maintain the desired angle, as described above. In the preferred embodiment, however, additional stop means 38 are included.

As stated above, it is desirous for an athletes forearm to maintain an angle of approximately 75 to 105 degrees, and most preferably about 90 degrees, with respect to the upper arm, as measured at the interior of the elbow. In the preferred form, stop means 28 comprising a rigid connector 54 are used to join the upper and lower arm engaging sections 30, 32 of one of the members 22, 24. Most preferably, the connector 54 is a triangular in shape, and formed of plastic along with the second arm engaging member 24 during molding. This connector 54, when the members 22, 24 are molded such that the upper and lower arm engaging sections 30, 32 are at an angle of about 90 degrees with respect to one another, takes on the form of a right triangle. It is, of course, possible to shape the stop means 28 in any of a variety of forms. Further, the stop means 28 need not be placed on the second arm engaging member 24, but may be on the first 22, or even both.

The stop means 28 can also comprise any of a number of other members. For example, if the brace 20 were made of a semi-rigid fabric material, it is possible for the stop means 28 to comprise a cord, interlocking hook, chain, or any of an infinite variety of members which connect the upper and lower arm engaging sections 30, 32 of one or both of the arm engaging members 22, 24, and prevent the angle between the forearm and upper arm from exceeding the desired angle at the elbow. When the members 22, 24 are mating halves which are made of plastic and interconnected with connecting means 26, positioning the stop means 28 on the second arm engaging member 24 (or the member closest to the body) prevents the other member 22 from being moved from the desired angle as well, as the members 22, 24 are connected. Most simply, the stop means 28 can comprise any member which aids in preventing the brace 20, and thus arm the brace 20 is used with, from being bent or manipulated such that the arm of the user is not within the desired position range.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A device for confining the angular movement of an elbow of an athlete, the arm including an upper arm section and a forearm section coupled at the elbow, comprising:

a brace having a first arm-engaging portion for engaging at least a portion of the upper arm and a portion of the forearm, and a second arm-engaging portion for engaging at least a portion of the upper arm and a portion of the forearm, each portion surrounding approximately half of the arm, the portions moveable from a first open position for acceptance of an arm therein, and a second closed position for substantially enclosing said arm; and stop means connected to said first and second arm-engaging portions for preventing the elbow of the athlete from extending to an angle of greater than about 105 degrees.

2. The device of claim 1, further including means for securing the first and second arm engaging members together in said closed position.

3. The device of claim 2, wherein said means for securing comprises at least one strap.

4. The device of claim 3, wherein said strap encompasses said brace and includes hook and loop fastening means.

5. The device of claim 1, wherein said stop means comprises a rigid member connecting forearm and upper arm engaging sections of at least one of said arm-engaging portions of said brace.

6. The device of claim 1, wherein said brace prevents the elbow of the athlete from extending to an angle of over about 90 degrees.

* * * * *